(12) United States Patent
Huang

(10) Patent No.: US 6,966,931 B2
(45) Date of Patent: Nov. 22, 2005

(54) ARTIFICIAL INTERVERTEBRAL DISC WITH RELIABLE MANEUVERABILITY

(75) Inventor: Shih-Shing Huang, Taipei (TW)

(73) Assignee: Tain-Yew Shi, Taipei (TW)

( * ) Notice: Subject to any disclaimer, the term of this patent is extended or adjusted under 35 U.S.C. 154(b) by 75 days.

(21) Appl. No.: 10/444,374

(22) Filed: May 21, 2003

(65) Prior Publication Data

US 2004/0236425 A1  Nov. 25, 2004

(51) Int. Cl.[7] ............................................... A61F 2/44
(52) U.S. Cl. ................................. 623/17.16; 623/17.11
(58) Field of Search ........................ 623/17.11, 17.12, 623/17.13, 17.14, 17.15, 17.16

(56) References Cited

U.S. PATENT DOCUMENTS

| | | | | |
|---|---|---|---|---|
| 3,875,595 A | * | 4/1975 | Froning | 623/17.12 |
| 4,309,777 A | * | 1/1982 | Patil | 623/17.13 |
| 5,375,823 A | * | 12/1994 | Navas | 623/17.15 |
| 5,549,679 A | * | 8/1996 | Kuslich | 623/17.12 |
| 5,674,294 A | * | 10/1997 | Bainville et al. | 623/17.16 |
| 5,674,296 A | * | 10/1997 | Bryan et al. | 623/17.16 |
| 6,187,043 B1 | * | 2/2001 | Ledergerber | 623/8 |
| 6,264,695 B1 | * | 7/2001 | Stoy | 623/17.16 |
| 6,582,466 B1 | * | 6/2003 | Gauchet | 623/17.11 |
| 6,893,465 B2 | * | 5/2005 | Huang | 623/17.12 |
| 2002/0035400 A1 | * | 3/2002 | Bryan et al. | 623/17.15 |
| 2004/0267369 A1 | * | 12/2004 | Lyons et al. | 623/17.16 |
| 2005/0085916 A1 | * | 4/2005 | Li et al. | 623/17.16 |

* cited by examiner

Primary Examiner—Paul B. Prebilic

(57) ABSTRACT

An artificial intervertebral disc includes an upper retaining member secured to an upper vertebra; a lower retaining member secured to a lower vertebra adjacent to the upper vertebra; and a nucleus member rotatably coupled between the upper and the lower retaining members, with the nucleus member having at least a cushioning filler selected from: gel, foam, elastomers, and shock-absorbing materials filled, formed or pre-formed in the nucleus member for making an artificial intervertebral disc as universally oriented, stably supported, reliably manipulated and minimally invasive.

12 Claims, 2 Drawing Sheets

ARTIFICIAL INTERVERTEBRAL DISC WITH RELIABLE MANEUVERABILITY

BACKGROUND OF THE INVENTION

U.S. Pat. No. 5,674,296 to Vincent Bryan et al. disclosed a human spinal disc prosthesis comprising a resilient body and concaval-convex elements partly surrounding the resilient body between adjacent vertebral bodies for retaining the resilient body between adjacent vertebral bodies in a patient's spine.

However, such a prior art has the following drawbacks:
1. The seal member (110) is attached to the supports (32, 34). During the bending or twisting movements of the patient's body, the seal member (110) may be easily separated or broken from the supports to lose its sealing effect, unable to limit the gasket (22) and the nuclear central portion (24) of the resilient body (20) within the concaval-convex means (30). The burst of the disc interior material may cause a "catastrophe" hazard to the patient's spine.
2. The resilient body (20) is retained within the concaval-convex means (30). It is lacking of any rotating mechanism to rotate the resilient disc body between the adjacent vertebrae, limiting a universal movement of the spinal vertebrae.
3. In order to stably restrict the resilient body (20) within the concaval-convex means (30), the peripheral aperture between the concaval-convex legs (42, 44) may be made as minimal as possible, thereby limiting the tilting angle when bending the patient's body.

The present inventor has found the drawbacks of the prior art and invented the present artificial intervertebral disc having improved maneuverability and reliability.

SUMMARY OF THE INVENTION

The object of the present invention is to provide an artificial intervertebral disc including an upper retaining member secured to an upper vertebra; a lower retaining member secured to a lower vertebra adjacent to the upper vertebra; and a nucleus member rotatably coupled between the upper and the lower retaining members, with the nucleus member having at least a cushioning filler selected from: gel, foam, elastomers, and shock-absorbing materials filled, formed or pre-formed in the nucleus member for making an artificial intervertebral disc as universally oriented, stably supported, reliably manipulated and minimally invasive.

DETAILED DESCRIPTION

Figure 1:
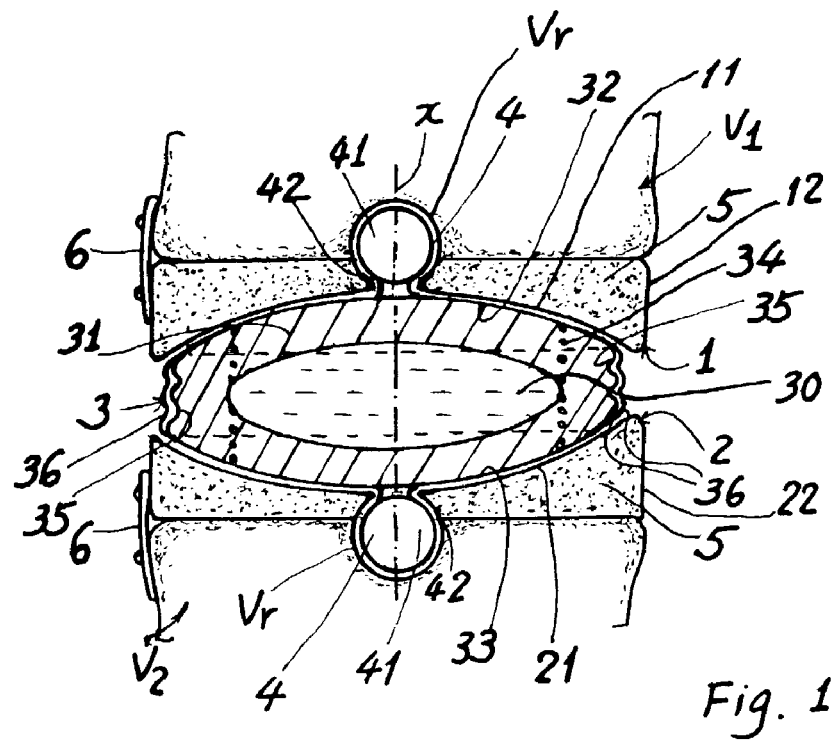
FIG. 1 is a sectional drawing of the present invention.

As shown in FIG. 1, the artificial intervertebral disc of the present invention comprises: an upper retaining member 1 secured to an upper vertebra $V_1$; a lower retaining member 2 secured to a lower vertebra $V_2$ adjacent to the upper vertebra $V_1$; and a nucleus member 3 rotatably coupled between the upper and the lower retaining members 1, 2.

The nucleus member 3 may be formed as oval shape or shallow cylindrical shape to be smoothly engageable in between the upper and lower retaining members 1, 2, but not limited in the present invention.

The nucleus member 3 is rotatably coupled with the upper and lower retaining members 1, 2 respectively with a pair of couplings 4, 4.

The nucleus member 3 defines a longitudinal axis X aligned with a center of each coupling 4.

Each coupling 4 includes a pivoting ball 41 formed on the nucleus member 3 and a socket 42 recessed in a central portion of either retaining member 1 or 2. The socket 42 may be protruded into each vertebra body $V_1$ or $V_2$ for a more stable fixation in a recess Vr in the vertebra. The nucleus member 3 is formed as a bladder having a cushioning filler 31 filled in the bladder.

The nucleus member 3 includes: an upper cup 32 generally spherically shaped and rotatably slidably engaging with a bottom cover 11 generally spherically shaped and formed on a bottom of the upper retaining member 1; a lower cup 33 generally spherically shaped and rotatably slidably engaging with a top cover 21 generally spherically shaped and formed on a top of the lower retaining member 2, and a side cover 35 circumferentially connecting and encasing the upper and lower cups 32, 33.

The side cover 35 may be formed as a bellows made of elastomers such as polyurethane. The cushioning filler 31 may be selected from: gel, foam, elastomers, viscous fluid and any other shock-absorbable materials filled in the bladder of the nucleus member 3.

Figure 2:
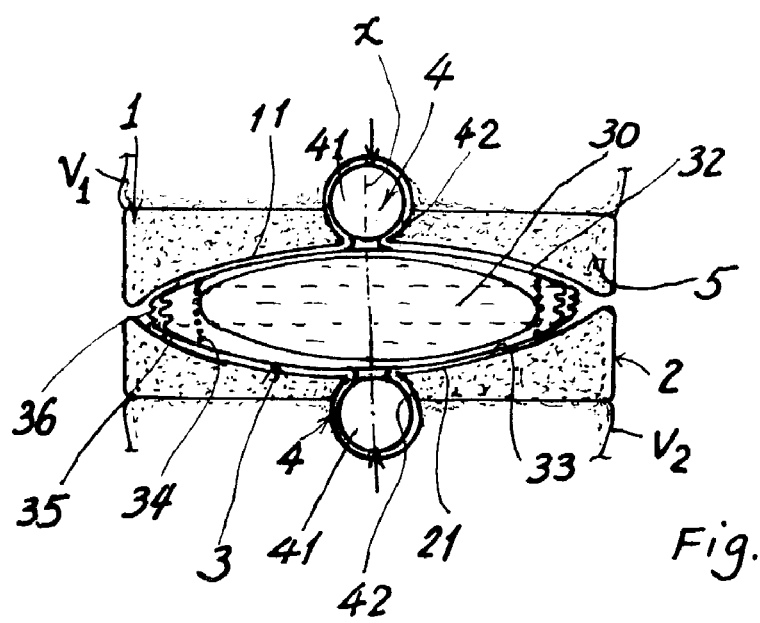
FIG. 2 is an illustration of the present invention when compressed for minimally invasive surgery.

If the cushioning filler 31 is selected from polyurethane, which may be preformed in the bladder. Or, the polyurethane may be a two-component system and be injected into the bladder of the nucleus member 3 which is previously compressed or squeezed when implanted and inserted in between two adjacent vertebrae as shown in FIG. 2 for minimally invasive surgery. After injection, the polyurethane will be foaming in situ to expandibly form a shock-absorbable cushioning member 3 of the present invention.

A daughter sac 30 prefilled with relatively soft materials such as gel, foam, low-density or low-hardness elastomer may be pre-set within a mother bladder of the nucleus member 3, whereby the exterior cushioning filler 31 of relatively hard materials such as high-density or high-hardness elastomer or foaming material is filled or foaming in situ in the bladder to circumferentially encapsulate the daughter sac 30 within the cushioning filler 31 in the mother bladder 3, thereby vividly simulating a nucleus of a true disc.

The "mother" cushioning filler 31 such as made of high-density polyurethane will provide the supporting strength for the adjacent vertebrae $V_1$, $V_2$; while the "daughter" sac 30 filled with low-density (low-hardness) PU or silicon elastomer, gel or foam therein will render better shock absorbing property to reliably play the disc role in between the vertebrae.

For reinforcing the supporting strength and stability of the disc of the present invention, a reinforcing tension spring 34 may be resiliently retained between the upper and lower cups 32, 33. The spring 34 once being "clad" in the elastomer or foam (such as PU) 31 foaming in situ in the nucleus member will synergetically reinforce the strength and stability of the disc. Namely, the tension spring 34 may play a role of a steel as existing in a reinforcing concrete (RC).

For preventing burst or breaking of the side cover 35 of the nucleus member 3, a reinforcing outermost side cover 36 such as made of polyethylene weave material may be secured between the upper and lower cups 32, 33 as circumferentially juxtapositionally surrounding the inner side cover 35.

The side covers 35, 36 should be made of flexible, stretchable materials having durable strength. So, weave materials of PE, nylon, or steel wire mesh may be selected in accordance with the present invention.

For positioning the daughter sac 30 in a central or core portion in the mother bladder, the sac 30 may be fastened to a middle position in the bladder such as secured in a middle position of the reinforcing tension spring 34. After foaming, the sac 30 is centrally positioned to better simulate a true disc.

Either upper or lower retaining member 1, 2 may be filled with biodegradable composition 5 therein. The fusion or bone growth from the upper or lower vertebra $V_1$, $V_2$ into the retaining member may substitute the void space as previously occupied by the biodegradable composition 5 which is now biodegraded and outwardly evacuated or released. The bone fusion into either retaining member 1, 2 may increase the stability and strength of the spine as implemented by the disc of the present invention.

The retaining member 1 or 2 may be secured to either vertebra $V_1$ or $V_2$ by a lug 6 having bolts respectively fastened to the lug 6 and to the vertebra $V_1$ or $V_2$.

Figure 5:
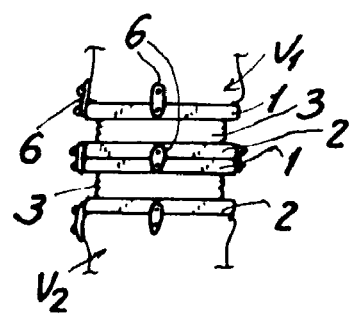
FIG. 5 is an illustration showing superimposing of two discs between adjacent vertebrae in accordance with the present invention.

For superimposition or overlapping purpose, plural discs of the present invention may be piled as fastened by lugs 6 as shown in FIG. 5 to provide a proper space or distance between adjacent vertebrae to be repaired.

Figure 4:
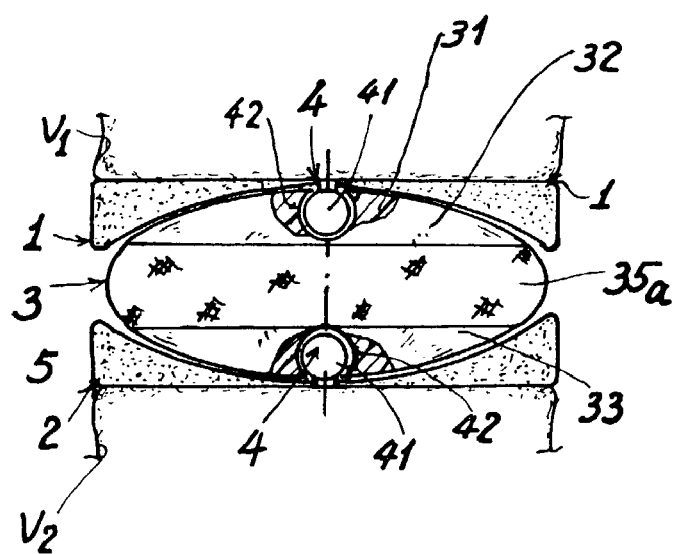
FIG. 4 is a sectional drawing showing another preferred embodiment of the present invention.

As shown in FIG. 4, the present invention is modified or simplified to be an oval-shaped bladder of the nucleus member 3 including a protective cover 35a preferably made of flexible steel wire mesh or flexible sheet of strong weave material circumferentially encasing the upper and lower cups 32, 33 of the nucleus member 3. The bladder 3 may be provided a cushioning filler 31 such as PU foaming in situ in the bladder.

The coupling 4 may also be modified to allow the ball 41 protruding from either retaining member 1 or 2 and to form the socket 42 to be recessed in either cup 32 or 33, to further make the disc as slim (or flat) as possible, especially adapted for minimally invasive surgery.

For smooth manipulation of the present invention, biocompatible lubricants may be provided into the revolving parts or interfaces such as: the ball and socket of the coupling 4; the interface between the cup 32 or 33 with the retaining members 1 or 2; or the aperture between the two side covers 35, 36.

The present invention is superior to the conventional intervertebral disc with the following advantages:

1. The nucleus member 3 as rotatably coupled between the two retaining members 1, 2 may allow a universal, flexible and rotatable movements of the spinal vertebrae for obtaining a comfortable maneuverability for the implant.
2. The covers 35, 36 always seal the bladder of the nucleus member 3 and are simultaneously rotatable with the bladder. Therefore, the covers 35, 36 will not be always subjected to high stress including shear, twisting, and tension forces, to thereby prolong their service life. The so-called "catastrophe" due to burst or breaking of conventional implant disc will be possibly prevented.
3. The bladder may be formed with the cushioning filler 31 by injection or by foaming in situ when previously squeezed to be a minimal volume and inserted in between the adjacent vertebrae, to thereby be especially recommendable for minimally invasive surgery.
4. Each coupling 4 plays double important roles, not only for rendering a universal movements of the disc; but also for "linking" the bladder of the nucleus member 3 in between the two retaining members 1, 2 (namely between the two adjacent vertebrae $V_1$, $V_2$) for preventing from dislocation or even burst of the nucleus member.

It is especially safe to prevent from injury to the spinal nerve.

All materials for making the elements of the present invention should be bio-compatible.

Figure 3:
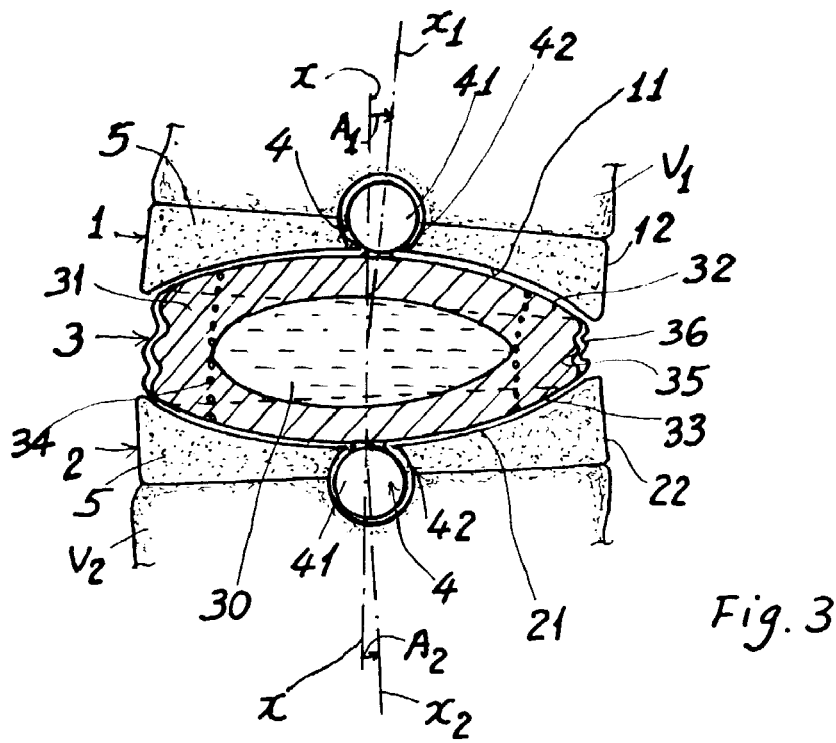
FIG. 3 shows a tilted situation of the present invention as provided in flexibly bent vertebrae.

The upper or lower retaining members 1 or 2 respectively corresponding to the vertebra $V_1$ or $V_2$ may be tilted in an acute angle $A_1$ or $A_2$ by biasing its axis $X_1$ or $X_2$ from the original axis X as shown in FIG. 3. The cup 32 or 33 and the contact surface of the cover 11, 21 of either retaining member 1, 2 are preferably made of stainless steel, Teflon-coated plate or other suitable materials to help a rotatable or engageable lubrication therebetween while still maintaining a proper strength and wear resistance.

The covers 35, 36 are preferably made as bellows for enhancing a better flexibility for the spinal movements.

The present invention may be modified without departing from the spirit and scope of the present invention. For simplifying purpose, the two coupling 4, 4 may also be modified to be a single one.

I claim:

1. An artificial intervertebral disc comprising:
   an upper retaining member adapted to be secured to an upper vertebra;
   a lower retaining member adapted to be secured to a lower vertebra adjacent to the upper vertebra; and
   a nucleus member rotatably coupled to said upper and lower retaining members by a least a coupling; said nucleus member including a daughter sac filled with a relatively soft cushioning filler in said daughter sac, and a mother bladder circumferentially encasing said daughter sac and having a relatively harder cushioning filler filled in said mother bladder for resiliently flexibly coupling said upper and lower retaining members; whereby said upper retaining member is universally resiliently coupled to said lower retaining member.

2. A disc according to claim 1, wherein said daughter sac is positioned at a central portion within said bladder of said nucleus member.

3. A disc according to claim 1, wherein said mother bladder is filled with the relatively hard cushioning filler selected from the group consisting of: high-density elastomers, foams, gels, and fluids; and said daughter sac is filled with relatively soft cushioning filler selected from: low-density elastomers, foams, gels and fluids.

4. A disc according to claim 3, wherein said elastomer is polyurethane (PU) selected from high density PU to low density PU.

5. A disc according to claim 1, wherein said nucleus member is formed as a shape selected from oval, spherical and cylindrical shapes, and includes a spherical-shaped upper cup rotatably slidably engaging with a spherical-shaped bottom cover of said upper retaining member; a spherical-shaped lower cup rotatably engaging with a spherical-shaped top cover of said lower retaining member; and said bladder of said nucleus member formed and secured between said upper and lower cups.

6. A disc according to claim 5, wherein said nucleus member further includes at least a side cover circumferentially sealing and connecting the upper and lower cups; said side cover made of flexible, stretchable and durable materials.

7. A disc according to claim 6, wherein said side cover is formed as a bellows.

8. A disc according to claim 5, wherein said nucleus member further includes at least a reinforcing tension spring retained between said upper and lower cups.

9. A disc according to claim 1, wherein said coupling includes a pivoting ball formed on said nucleus member and a socket recessed in one said retaining member.

10. A disc according to claim 1, wherein said coupling includes a pivoting ball protruding from said nucleus member, and a socket formed in said retaining member and in said vertebra for rotatably engaging said pivoting ball.

11. A disc according to claim 5, wherein said nucleus member includes a flexible inner side cover circumferentially sealing the upper and lower cups; and an outermost flexible side cover juxtapositionally circumferentially encasing said inner side cover.

12. A disc according to claim 5, wherein each said cup and each said cover of said retaining member is respectively formed with a lubricating and wear-resistant surface therein for a smooth slidable rotatable engagement between said cup and said retaining member.

* * * * *